US005801828A

United States Patent [19]
Collins

[11] Patent Number: 5,801,828
[45] Date of Patent: Sep. 1, 1998

[54] APPARATUS AND METHOD FOR FLUORESCENCE SPECTROSCOPY OF REMOTE SAMPLE

[75] Inventor: Russell L. Collins, Austin, Tex.

[73] Assignee: Detections Unlimited, Inc., Austin, Tex.

[21] Appl. No.: 748,763

[22] Filed: Nov. 14, 1996

[51] Int. Cl.$^6$ ............................................. G01N 21/64
[52] U.S. Cl. ...................... 356/318; 356/417; 250/461.1
[58] Field of Search .................................. 356/317, 318, 356/417; 250/458.1, 459.1, 461.1, 461.2

[56] References Cited

U.S. PATENT DOCUMENTS

| | | | |
|---|---|---|---|
| 3,814,939 | 6/1974 | Parker et al. | 250/373 |
| 4,018,530 | 4/1977 | Hirschfeld | 356/85 |
| 4,200,801 | 4/1980 | Schuresko | 250/458.1 |
| 4,247,770 | 1/1981 | Welch | 356/318 |
| 4,461,573 | 7/1984 | Lucht et al. | 356/318 |
| 4,490,040 | 12/1984 | Lucht et al. | 356/318 |
| 4,575,241 | 3/1986 | Demers et al. | 356/316 |
| 4,591,267 | 5/1986 | Demers et al. | 356/316 |
| 4,675,300 | 6/1987 | Zare et al. | 436/172 |
| 4,798,463 | 1/1989 | Koshi | 356/318 |
| 4,900,933 | 2/1990 | Nestor et al. | 250/458.1 |
| 4,946,279 | 8/1990 | Ohkubo | 356/318 |
| 5,190,857 | 3/1993 | Allen et al. | 435/7.21 |
| 5,202,744 | 4/1993 | Louis | 356/417 |

FOREIGN PATENT DOCUMENTS

296259  6/1987  European Pat. Off. .

*Primary Examiner*—F. L. Evans
*Attorney, Agent, or Firm*—Russell D. Culbertson; Shaffer & Culbertson

[57] ABSTRACT

A fluorescence spectrometer (10) includes an excitation light source (12) and an excitation light input mirror (14) for reflecting excitation light produced by the light source and directing the light along a spectrometer light path (24). A reflecting arrangement (16) receives the excitation light directed along the spectrometer light path (24) and focuses the excitation light along a sample light path (20) to a distant focal point (32) at which a sample may be located. The reflecting arrangement (16) also serves to collect light emitted or reflected from the sample at the distant focal point (32) and to reflect the collected or returned light back along the spectrometer light path (24) in a direction opposite to the direction of the excitation light. The excitation light input mirror (14) is adapted to pass wavelengths in a target fluorescence spectrum and, therefore, wavelengths within this range pass along the spectrometer light path (24) through the excitation light input mirror (14) to a returned light detecting arrangement (18) which provides an output indicating the relative intensity of a desired wavelength constituent of the returned light. The excitation light may be chopped at a frequency different from the frequency at which background light is produced. Where the excitation light is chopped or produced intermittently, the signal produced in response to the background light at the returned light detecting arrangement (18) may be removed electronically to provide an output resulting solely from the excitation light incident upon the sample.

25 Claims, 6 Drawing Sheets

Wavelength (nm)

APPARATUS AND METHOD FOR FLUORESCENCE SPECTROSCOPY OF REMOTE SAMPLE

BACKGROUND OF THE INVENTION

This invention relates to spectroscopy, and particularly to an apparatus for performing fluorescence spectroscopy of a sample which may be at a location remote from the apparatus. The invention also includes a method of performing fluorescence spectroscopy.

Many organic compounds fluoresce when illuminated by electromagnetic radiation at wavelengths which are absorbed by the compound. The fluorescence radiation is of a longer wavelength than that of the exciting radiation and this fluorescence wavelength is characteristic of the particular compound. Thus, the fluorescence characteristic of a material may be used to identify a particular material. Fluorescence spectroscopy for the purpose of identifying a given sample is commonly performed on samples in solution, and reference fluorescence spectra have been published for many compositions in solution.

While fluorescence spectroscopy is useful for identifying materials in solution, prior fluorescence spectrometers had inherent limitations which restricted the applicability of the technique. For example, the low signal-to-noise ratio in prior fluorescence spectrometers rendered the devices unsuitable for use in identifying materials in solid form. Also, prior fluorescence spectrometers required that a sample be in a structure which completely isolated the sample from background light. Any background light illuminating the sample interfered with the device and caused the device to produce unpredictable and unusable results. These limitations of prior fluorescence spectrometers restricted fluorescence spectroscopy to laboratory settings.

SUMMARY OF THE INVENTION

It is an object of the invention to provide a fluorescence spectrometer which overcomes the above-described limitations and others associated with prior fluorescence spectrometers. More specifically, it is an object of the invention to provide a fluorescence spectrometer and method of spectroscopy which may be used for samples in either a solid or liquid form without requiring that the sample be isolated from the environment or be in close proximity to the spectrometer optics.

In order to accomplish these objects, the apparatus according to the invention includes a unique optical system for directing excitation light and collecting the fluorescent light emitted from the sample in response to the excitation light. The invention also includes a unique excitation light source which improves the signal-to-noise ratio of the apparatus. In the preferred form of the invention, the apparatus is specifically adapted for emitting a particular wavelength excitation light in the absorption range of a material to be detected, and the device may be used to indicate the presence or absence of the material. This specific excitation light form of the invention is particularly applicable for providing an indication of the presence of illegal drugs. The fluorescence spectrometer and method of spectroscopy according to the invention may also be used for general spectroscopic analysis.

The apparatus includes an excitation light source for producing excitation light of the desired wavelength or spectrum and directing the excitation light to an input mirror. The input mirror is adapted to reflect at least a portion of the excitation light and direct the reflected light along a spectrometer light path. The excitation light input mirror is also adapted to allow light within a target spectrum to pass therethrough along the spectrometer light path. A reflector arrangement receives the excitation light along the spectrometer light path and focuses the excitation light along a sample path to a sample location. The reflector arrangement also collects light emitted from the sample location traveling back along a path reciprocal to the sample path and reflects collected light back along the spectrometer light path.

The collected light returns along the spectrometer light path and at least a portion of the collected light which is in the target spectrum passes through the excitation light input mirror and is received at a detecting arrangement or means. The returned light detecting means provides an indication of the relative intensity of a desired constituent of the returned light. The presence of a certain fluorescence wavelength or spectrum at the detecting means in response to the excitation light at a certain wavelength represents a fluorescence signature to indicate a particular substance is present at the sample location.

The reflector arrangement for focusing the excitation light to the sample location and collecting fluorescent light from the sample location preferably comprises a paraboloidal mirror positioned along the spectrometer light path and an ellipsoidal mirror. The paraboloidal mirror's focal point is positioned at a near focal point of the ellipsoidal mirror and reflects light from the spectrometer light path to the ellipsoidal mirror. The ellipsoidal mirror reflects and focuses the excitation light along a sample light path to a distant focal point of the ellipsoidal mirror. The sample location may comprise any position within the light path between the ellipsoidal mirror and the distant focal point, or in the light path beyond the focal point; however, the preferred sample location is the distant focal point.

Fluorescent light emitted from the sample location in response to the excitation light travels back along the sample light path to the ellipsoidal mirror which serves as a collector for collecting this emitted fluorescent light. The ellipsoidal mirror reflects the collected light, including fluorescent light emitted from the sample in response to the excitation light, back to the paraboloidal mirror which reflects the collected light back along the spectrometer light path. The reflecting arrangement including the paraboloidal mirror and ellipsoidal mirror may be termed a "confocal" arrangement since the focus of the paraboloidal mirror is sited at one of the foci of the ellipsoidal mirror.

This "confocal" arrangement has several advantages. First, the ellipsoidal mirror is capable of focusing high intensity light at a sample point which is some distance from the mirror. Larger ellipsoidal mirrors may be used to increase the sample distance from the mirror. Secondly, by receiving the fluorescent light along a path reciprocal to the excitation light, the ellipsoidal mirror receives the highest intensity fluorescent light from the sample and receives such light across a large solid angle. Thus, the ellipsoidal mirror collects a relatively large amount of the total fluorescent light emitted from the sample in response to the excitation light.

The excitation light source includes a lamp capable of producing excitation light at the desired wavelengths, preferably along with means for limiting the wavelength constituents in the excitation light, and optics for focusing the excitation light in a collimated or parallel beam to the excitation light input mirror. Filters may be used as the excitation light wavelength limiting means to filter the light and produce an excitation light having the desired wavelengths. Where filters are used, the apparatus preferably includes a cooling arrangement for cooling the filter or filters. Alternatively, the wavelength limiting means in the excitation light source may include a monochromator.

The returned light detecting means includes a photomultiplier tube and wavelength limiting means for selecting a desired wavelength of returned light, or band of return light, to pass to the photomultiplier tube. As in the excitation light source, the wavelength limiting means in the returned light detecting means may comprise a filter arrangement, and may alternatively include a monochromator.

In the preferred form of the invention, the apparatus includes an arrangement for producing the excitation light at an amplitude which is varied at a desired frequency. In this preferred form of the invention, the excitation light source includes a lamp and cycling means for energizing the lamp on and off at a desired frequency. The frequency at which the excitation light is chopped (turned on and off) is chosen to be different from the frequency at which background light or other contaminating light may be produced. Also, the returned light detecting means is adapted to be sensitive only to light chopped at the frequency corresponding to the frequency at which excitation light is chopped by the excitation light source.

Although the chopped or intermittent excitation light may be produced with a rotating wheel having alternate opaque portions and open portions, the preferred form of the invention comprises an electronic cycling arrangement for producing the intermittent excitation light. The electronic cycling arrangement comprises an operating power supply, a control transistor arrangement, and a switching transistor arrangement. The switching transistor is used to produce a switching signal which controls whether the control transistors are biased to conduct or are in a nonconducting condition. When biased to conduct, the control transistors apply operating power from the operating power supply to the lamp. The preferred apparatus may also include a high voltage power supply for initially igniting the lamp at start up.

The apparatus according to the invention has several advantages over the prior art devices. One advantage is that the apparatus may perform fluorescence spectroscopy on either liquid or solid samples. Perhaps most importantly, the optics and preferred intermittent excitation light source of the apparatus allow the device to be used to identify samples which are not isolated from background light. Furthermore, the samples do not have to be in close proximity to the excitation light focusing optics of the apparatus. Depending upon the size of the ellipsoidal mirror, the sample location may easily be 16 inches away from the ellipsoidal mirror.

There are many applications for the fluorescence spectrometer according to the invention. One application for the device is for identifying or detecting illicit drugs such as cocaine, met-amphetamine, morphine, and others. The apparatus may provide a positive identification for a drug which is present in only very minute quantities. This positive identification without an invasive search can provide probable cause for law enforcement officers to conduct further searching.

These and other objects, advantages, and features of the invention will be apparent from the following description of the preferred embodiments, considered along with the accompanying drawings.

DESCRIPTION OF THE PREFERRED EMBODIMENTS

Figure 1:
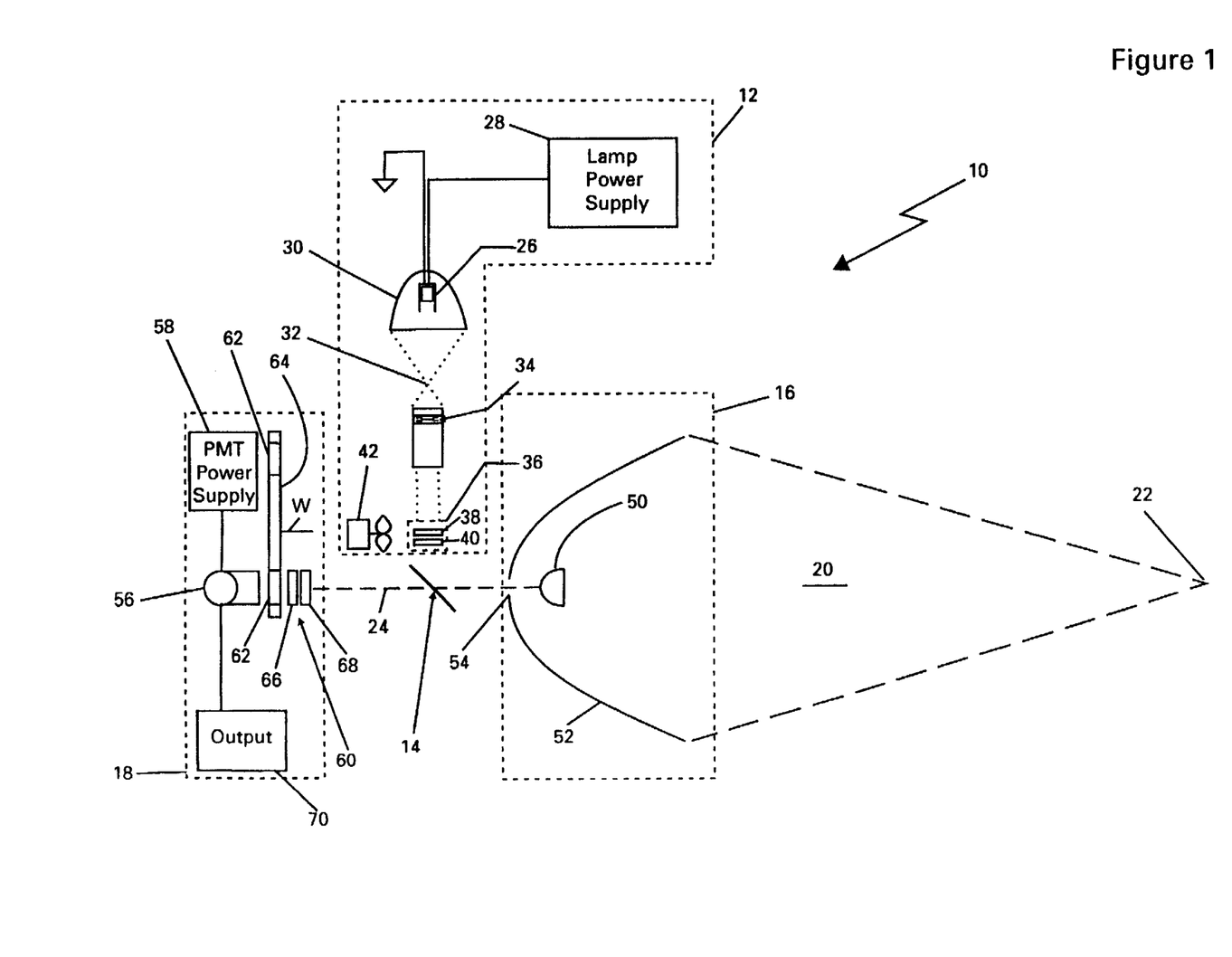
FIG. 1 is a diagrammatic representation of a fluorescence spectrometer embodying the principles of the invention.

FIG. 1 illustrates one preferred form of a fluorescence spectrometer 10 embodying the principles of the invention. The fluorescence spectrometer 10 includes an excitation light source 12, an excitation light input mirror 14, excitation light reflecting means 16, and returned light detecting means 18. The spectrometer 10 is adapted to perform fluorescence spectral analysis on a sample positioned within a sample light path 20, and preferably at a sample location 22.

In operation, excitation light from the excitation light source 12 is reflected from the excitation light input mirror 14 to direct the excitation light along a spectrometer light path 24. The excitation light reflecting means 16 receives the light along the spectrometer light path and focuses the light along the sample light path 20 to the sample location 22 some distance from the excitation light reflecting means 16. Light in a target fluorescence spectrum and other light emitted or reflected from the sample location 22 or within the sample light path 20 travels back along the sample light path to the excitation light reflecting means 16 which collects the light and reflects the collected light back along a spectrometer light path 24. The collected light travels along the spectrometer light path 24 through the excitation light input mirror 14 to the returned light detecting means 18. The returned light detecting means 18 produces an indication of the relative intensity of one or more desired wavelength constituents of the collected light.

Although for purposes of illustration the apparatus 10 is described in terms of excitation and collected "light", those skilled in the art will readily appreciate that the "light" may comprise any electromagnetic radiation and is not limited to electromagnetic radiation in the visible light range. In fact, one preferred application of the fluorescence spectrometer 10 is in detecting the presence of illicit drugs and uses an excitation light having a wavelength of 254 nanometers, which is in the ultraviolet range.

In the preferred form of the invention, the excitation light reflecting means 16 serves both to focus the excitation light to the distant optimum sample position 22 and collect the emitted fluorescent light. A separate collecting arrangement may be used within the scope of the invention. However, the separate focusing and collecting arrangement takes up significantly more space in order to collect emitted light along a large solid angle.

In the illustrated form of the invention shown in FIG. 1, the excitation light source 12 includes a lamp 26 powered by a lamp power supply 28. Input light emitted from the lamp 26 is collected by ellipsoidal mirror 30 and focused to a distant focal point 32. The input light diverging after the distant focal point 32 is collimated by the objective lens 34 and then the collimated beam is directed to excitation light wavelength limiting means 36.

The excitation wavelength limiting means 36 is adapted to block electromagnetic radiation at undesired wavelengths and to pass on as the excitation light only light at a desired wavelength or in a desired wavelength range. In the illustrated form of the invention, the excitation wavelength limiting means 36 comprises a filter arrangement. For example, the filter arrangement may comprise a band pass filter 38 adapted to pass electromagnetic radiation in a certain range and may also include other optical devices such as dielectric mirror 40 for reflecting certain wavelengths. Where filters are used to limit the wavelength constituents in the excitation light, the heat produced by blocking or reflecting portions of the input light may require a blower 42 or other suitable cooling arrangement for cooling the filter 38 and dielectric mirror 40.

The excitation light generated by the excitation light source 12 in the illustrated form of the invention comprises a collimated beam directed to the input mirror 14 at an angle to the spectrometer light path 24. The excitation light preferably comprises light only at wavelengths required for exciting the characteristic fluorescence of a particular substance under investigation. However, the excitation light may include a broad range of wavelength constituents.

In alternative forms of the invention, the excitation wavelength limiting means 36 may include a monochromater. Using a monochromater as the excitation wavelength limiting means 36 allows the wavelength constituents of the excitation light to be varied to analyze different samples. This ability to analyze different samples makes the device 10 well suited for general fluorescence spectroscopy applications. However, the use of filters to limit the excitation light wavelengths to a desired range allows the excitation light source 12 to be smaller, reducing the overall size of the device 10 and making it more portable. Also, those skilled in the art will readily appreciate that certain light sources may have a narrow enough light emission range that wavelength limiting means are not required. The excitation light source 12 according to the invention need only produce excitation light having the desired wavelength or wavelengths which are absorbed by the sample material to produce the signature fluorescence.

The excitation light input mirror 14 may be any suitable mirror or reflecting device which is capable of reflecting the excitation light at the particular excitation light wavelengths. The excitation light input mirror 14 must also be capable of passing electromagnetic radiation at wavelengths within a target fluorescence spectrum. The target fluorescence spectrum includes electromagnetic radiation at wavelengths which are characteristic of the fluorescent emissions produced by the particular sample under investigation. For general applications of the apparatus 10, the excitation light input mirror 14 may comprise a partially silvered mirror which reflects some fraction of all incident wavelengths and allows the remainder of the light at all wavelengths to pass therethrough unreflected. This partially silvered mirror form of the invention is suitable for the general application of the device 10, which uses a monochromater as an excitation wavelength limiting means 36 to produce excitation light within a broad range of wavelengths.

In the specific application form of the invention where the excitation wavelength limiting means 36 is fixed to one wavelength or range of wavelengths for the excitation light, the excitation light input mirror 14 may comprise a dichroic mirror turned to reflect only the excitation wavelengths. In any event, the mirror 14 must reflect at least a portion of the incident excitation light and pass at least a portion of each wavelength within the target fluorescence spectrum.

The excitation light reflecting means 16 preferably comprises a paraboloidal mirror 50 and ellipsoidal mirror 52. The focal point of the paraboloidal mirror 50 is positioned at the near focal point of the ellipsoidal mirror 52 and is positioned on the spectrometer light path 24 to receive excitation light reflected from the excitation light input mirror 14. The sample light path 20 comprises the path of light reflected from the ellipsoidal mirror 52 to the preferred sample position 22 which coincides with the distant focal point of the ellipsoidal mirror. In the illustrated form of the invention in which the spectrometer light path 24 is open space as opposed to a conduit such as an optical fiber, the ellipsoidal mirror 52 includes at its apex an opening 54 coinciding with the spectrometer light path.

The preferred returned light detecting means 18 comprises a photomultiplier tube 56 having a suitable power supply 58 and returned light wavelength limiting means 60 for allowing only a selected wavelength constituent of returned light to pass to the photomultiplier tube. Output device 70 receives the signal from the photomultiplier tube 56 and produces a desired output to the device operator indicating the relative intensity of the target fluorescence wavelength. In the form of the invention shown in FIG. 1, the returned light wavelength limiting means 60 comprises one or more filters 62. Where the device includes multiple filters 62, each filter is adapted to pass a different target fluorescence wavelength. The filters 62 are arranged about the periphery of a wheel structure 64 and the wheel rotated about wheel axis W to position the desired filter in the spectrometer light path 24 to the photomultiplier tube 56. The apparatus 10 may alternatively include only one fixed or interchangeable filter 62. The filter form of the returned light wavelength limiting means 60 may also require a specific filter 66 such as a dielectric mirror tuned to reject returned light at a particular wavelength such as the wavelength of the excitation light, for example. The filtering arrangement may also include a solar-blind filter 68 which blocks certain background light.

The photomultiplier tube 56 is shown in FIG. 1 as an example of a device which may produce an indication of the relative intensity of light or electromagnetic radiation incident upon the device. Those skilled in the art will readily appreciate that any device which produces such an indication of relative intensity of incident electromagnetic radiation may be used within the scope of the invention. Suitable devices may include photocells and charge coupled detectors, for example. The indication produced by the output device 70 may be visual or auditory, for example. A visual indication may be provided by a light (not shown) which operates when the target wavelength intensity is above a certain point, or a meter (also not shown) which provides a quantitative display. An auditory signal may be a sound having a pitch which changes to indicate the relative intensity of the target wavelength.

Referring still to FIG. 1, the lamp power supply 28 may produce a constant output to operate the lamp 26 continuously and produce a constant input light for the device 10. However, in the preferred form of the invention, the amplitude of the excitation light is varied or chopped at a desired frequency. The excitation light is preferably chopped at a frequency different from the frequency at which background light is produced. By synchronizing the photomultiplier tube 56 output signal with the excitation light, and comparing the photomultiplier tube 56 output at the times in which no excitation light is produced and at times in which the excitation light is produced, any signal from background light may be eliminated, leaving only the true signal produced in response to the excitation light incident on the sample. Thus, the chopped or intermittent excitation light increases the signal-to-noise ratio of the device 10. In the preferred form of the invention, a lock-in amplifier (not shown) is used in connection with the output device 70 to restrict the band width of the photomultiplier tube 56 signal which is amplified, thereby decreasing Nyquist noise.

Figure 2:
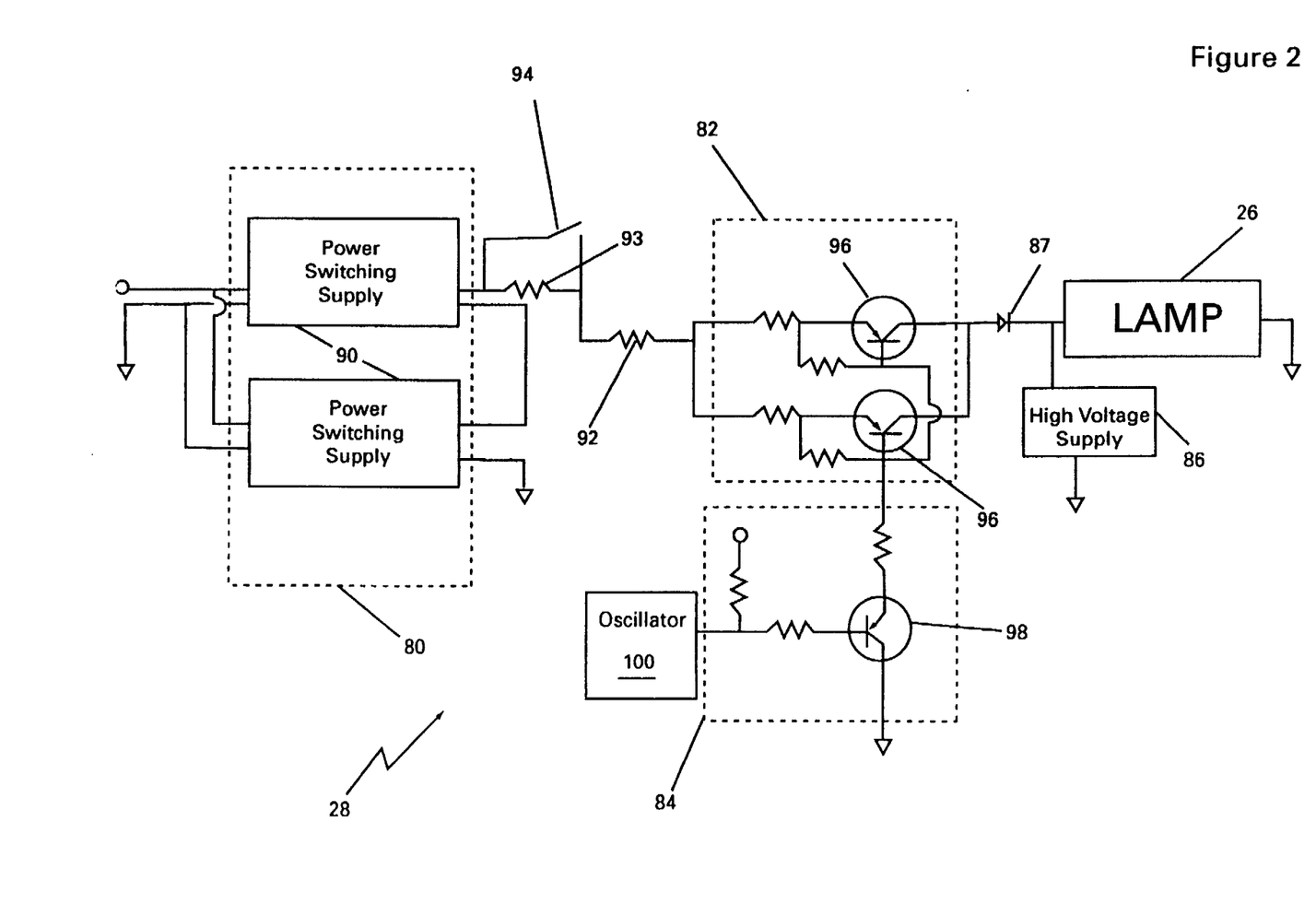
FIG. 2 is an electrical schematic diagram of an intermittent light source embodying the principles of the invention.

The intermittent excitation light may be produced mechanically using a wheel (not shown) having alternating opaque and open areas at its periphery and placing the wheel in an appropriate location along the excitation light path. The wheel may be driven at a speed to produce a desired chopped frequency. However, the preferred form of the invention produces the chopped or intermittent light by a light cycling lamp power supply 28 shown in FIG. 2. Referring to FIG. 2, the light cycling power supply 28 comprises an operating power supply 80, control means 82 and switching means 84. The lamp power supply 28 also includes a high voltage input source 86 for momentarily producing a high voltage to ignite the lamp 26 at the start of operation. Diode 87 isolates the remainder of the circuit from the high voltage source 86.

The operating power supply 80 is connected to receive alternating current and comprises switching power supplies 90, producing a desired d.c. output. The operating power supply 80 is connected to the control means 82 through current limiting resistors 92 and 93 and a shorting switch 94 which is closed to reduce resistance at start up. The use as a portable device may require reduction of the power level of the lamp, in which case shorting switch 94 is opened after the lamp starts. The preferred control means 82 comprises two transistors 96, both having their base connected to the emitter of a switching transistor 98 of the switching means 84. A TTL level input to the base of the switching transistor 98 causes the switching transistor to conduct to produce a switching input signal which biases both of the control transistors 96 to conduct and apply the operating voltage from operating power supply 80 to the lamp 26. When the TTL level signal goes to "low" at the base of the switching transistor 98, the control transistors 96 are biased to a nonconducting condition blocking the voltage and current to the lamp 26. The TTL level signal to the switching transistor 98 may be produced by any suitable means and preferably a 555 astable oscillator 100.

In the preferred form of the invention, which is specifically adapted for detecting illicit drugs, the lamp 26 may comprise a 100 watt mercury short-arc lamp, such as the model HBO100W/2 manufactured by the Osram Company. This lamp produces large amounts of useful radiation at a wavelength of 253.7 nanometers. Electromagnetic radiation at this wavelength is useful as an excitation light which is absorbed by certain illicit drugs. Although this lamp is intended for d.c. operation, the cycling power supply 28 shown in FIG. 2 may be used to pulse the lamp over a range of frequencies of about 1,000 to 9,500 Hertz with the voltage input to the lamp representing substantially a square wave. In the preferred special application of the invention for detecting illicit drugs, the lamp is pulsed at a frequency of approximately 2500 Hertz.

In a test arrangement, the device 10 was set up as shown in FIG. 1 with the exception being that the filter wheel 64 with specific filters 62 was replaced with a ⅛ meter monochromater. The solar blind filter 68 was retained and the beam of light along the spectrometer light path was brought to a focus at the entrance slit of the monochromater by a quartz lens having a 25 millimeter focal length. The photomultiplier tube power supply supplied a drive voltage which was multiplied by 139. The sensitivity of the photomultiplier tube increases exponentially with the drive voltage. The output from the photomultiplier tube was collected with a personal computer for analysis and printout, and the averaging time at each point, spaced by 1 nanometer, was 3 seconds. The bandpass filter 38 in the test device was centered at 253.7 nanometers and the dielectric mirror 40 was tuned to reflect the interfering 334 nanometer light produced by the lamp 26. This test arrangement was used to produce the spectra shown in FIGS. 3A, 3B, 4A, 4B, 5, and 6.

Figure 3A:
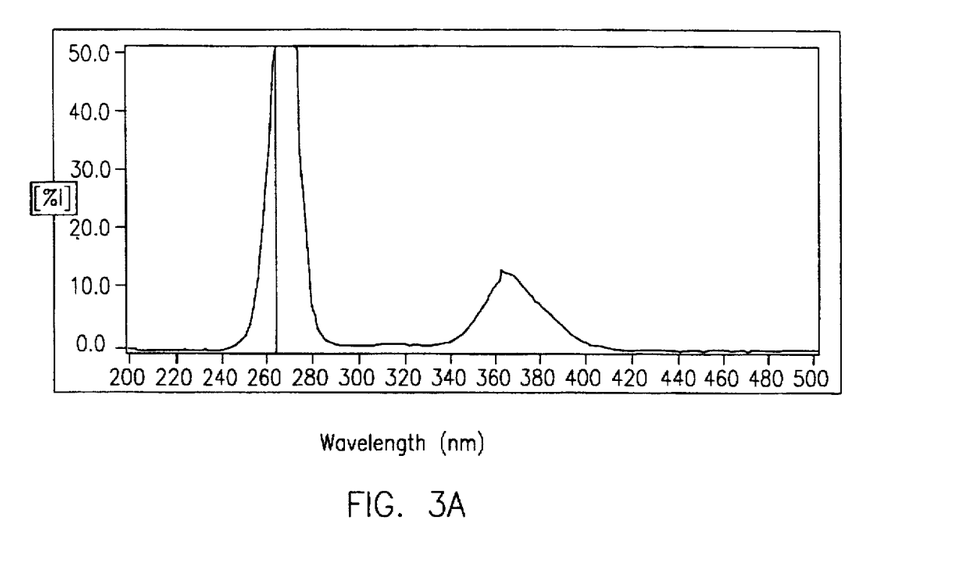
FIG. 3A is a graph showing the fluorescence spectrum produced by cocaine using an apparatus embodying the principles of the invention with a +6 volt drive voltage on the photomultiplier tube.
Figure 3B:
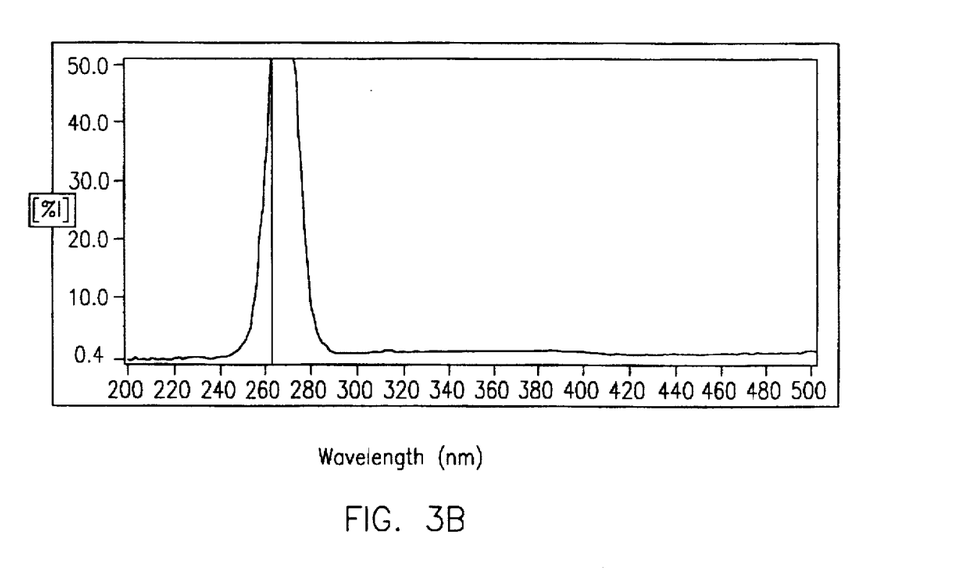
FIG. 3B is a graph showing the fluorescence spectrum produced by the same apparatus used to produce FIG. 3A, but with the device focused on open space with a photomultiplier tube drive voltage of +6 volts.

FIG. 3A shows the fluorescence spectrum of cocaine powder rubbed onto a piece of wool cloth. In this example, the monochromater was somewhat out of calibration and the excitation peak shown at 265 nanometers is actually 253.7 nanometers. Although the input mirror 14 reflects light at the excitation wavelength, the excitation light is scattered within the device 10 and some of this scattered excitation light reaches the photomultiplier tube 56 to produce the excitation peak appearing in the figures. The fluorescence peak at 365 nanometers is characteristic of cocaine. FIG. 3B shows the response of the device with the cocaine sample removed and the light reflecting means 16 directed to empty space. For both of these tests, the drive voltage for the photomultiplier tube was 6 volts.

Figure 4A:
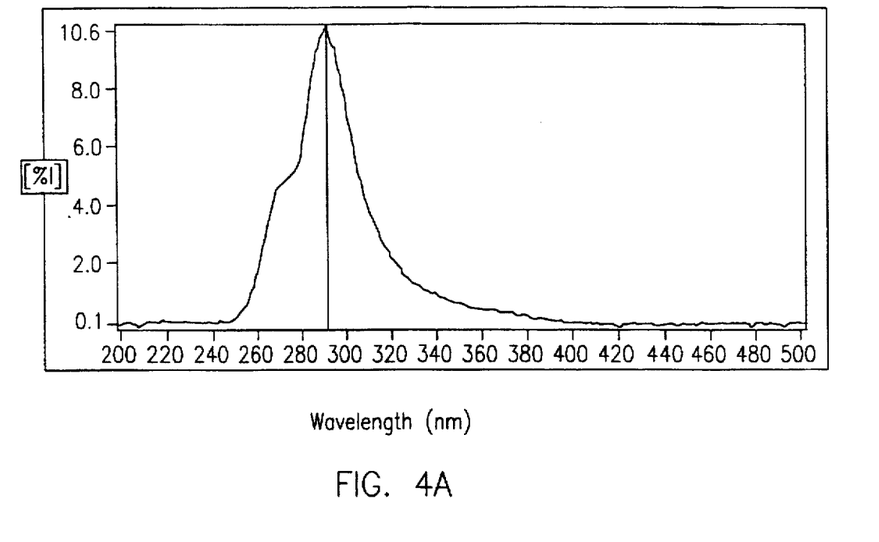
FIG. 4A is a graph showing the fluorescence spectrum produced by met-amphetamine using an apparatus embodying the principles of the invention with a +4 volt drive voltage on the photomultiplier tube.
Figure 4B:
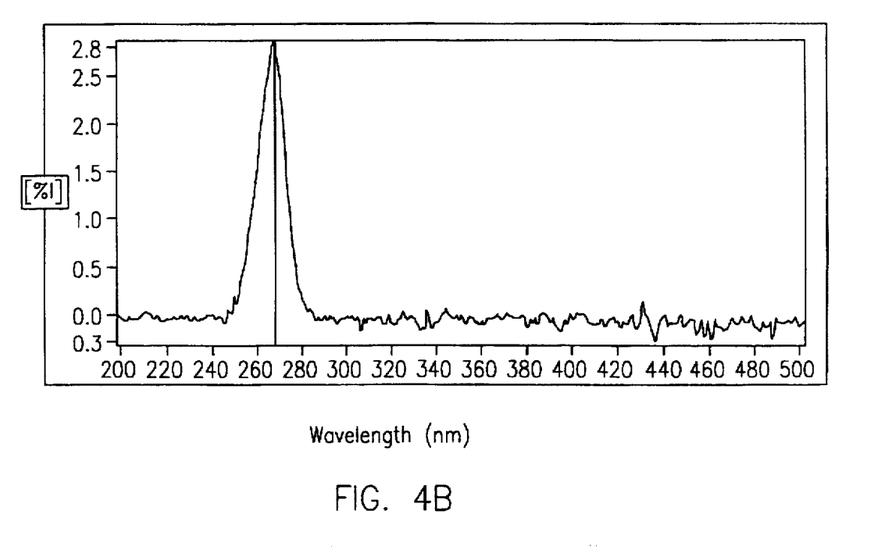
FIG. 4B is a graph showing the fluorescence spectrum produced by the same apparatus used to produce FIG. 4A, but with the device focused on open space with a +4 volt drive voltage on the photomultiplier tube.

FIG. 4A shows the fluorescence of met-amphetamine at 289 nanometers being somewhat stronger than the intensity of the excitation light at 253.7 nanometers. The excitation light shows up as a shoulder on the left side of the fluorescence peak. FIG. 4B shows the response of the device 10 with the reflecting arrangement 16 focused on open space. The spectra shown in FIGS. 4A and 4B were each produced with a 4 volt drive voltage to the photomultiplier tube.

Figure 5:
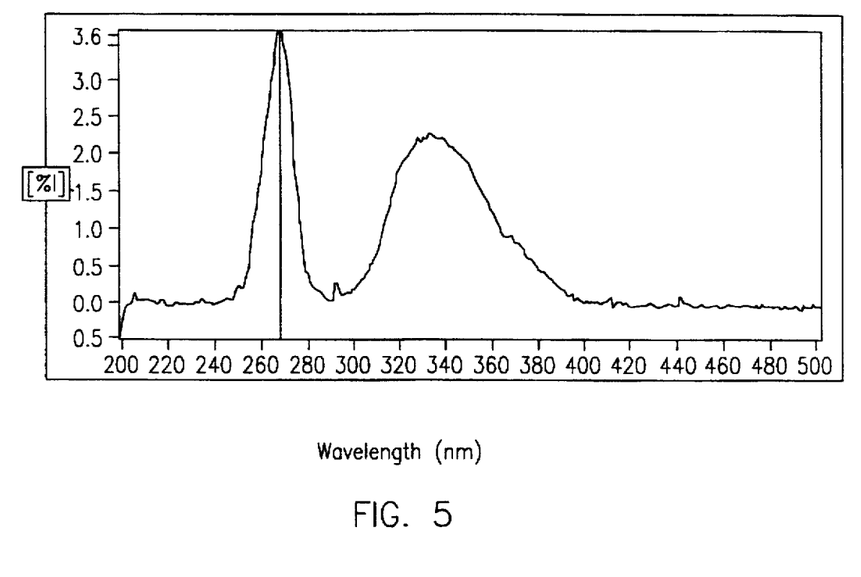
FIG. 5 is a graph showing the fluorescence spectrum produced by morphine using an apparatus embodying the principles of the invention with a photomultiplier tube drive voltage of +4 volts.
Figure 6:
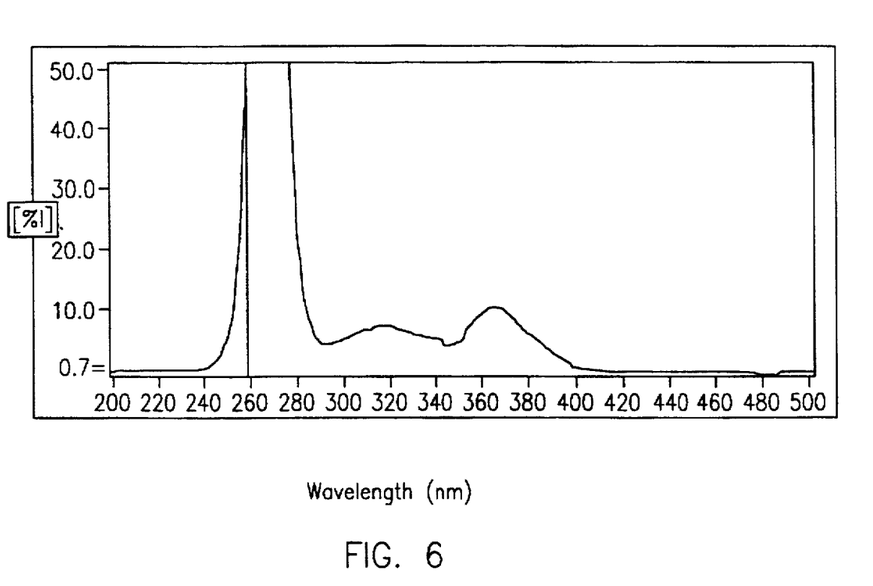
FIG. 6 is a graph showing the fluorescence spectrum produced by cocaine through two layers of thin polyethylene, using a +6 volt photomultiplier tube drive voltage.

FIG. 5 shows the signal produced by morphine at a photomultiplier tube drive voltage of 4 volts. FIG. 6 shows the response of the device 10 using a sample of cocaine on wool through two layers of thin polyethylene. The drive voltage to the photomultiplier tube 56 was 6 volts. The intensity of the fluorescence response from cocaine falls from approximately 15 percent to approximately 11 percent when the sample is taken through the two layers of thin polyethylene.

The above described preferred embodiments are intended to illustrate the principles of the invention, but not to limit the scope of the invention. Various other embodiments and modifications to these preferred embodiments may be made by those skilled in the art without departing from the scope of the following claims. For example, the spectrometer light path need not be open space, but may be a suitable conduit such as an optical fiber. Also, although the presence of a single wavelength of light may represent a fluorescence signature which indicates the presence of a particular compound at the sample location, a characteristic fluorescence response may comprise a band of wavelengths, typically having a peak at a certain wavelength and having wavelengths adjacent to the peak lowering in intensity in a characteristic manner. This characteristic band of wavelengths may, therefore, be used to indicate the presence of a particular compound.

I claim:

1. A fluorescence spectrometer comprising:
   (a) an excitation light source;
   (b) an excitation light input mirror for reflecting excitation light produced by the excitation light source and directing the excitation light along a spectrometer light path, the excitation light input mirror adapted to allow at least a portion of a target fluorescence spectrum to pass therethrough;
   (c) a parabaloidal mirror positioned on the spectrometer light path to receive the excitation light reflected by the excitation light input mirror;
   (d) an ellipsoidal mirror having the focus of the parabaloidal mirror at a near focal point thereof, the ellipsoidal mirror being in position to receive excitation light reflected by the parabaloidal mirror and focus the excitation light to a distant focal point; and
   (e) returned light detecting means positioned on the spectrometer light path in position to receive returned light and providing an output indicating the intensity of a desired wavelength constituent of the returned light, the returned light including light within the target fluorescence spectrum which is reflected by the ellipsoidal mirror and parabaloidal mirror back along the spectrometer light path and passed through the excitation light input mirror.

2. The apparatus of claim 1 wherein the excitation light source further includes:
   (a) light cycling means for chopping the excitation light intermittently at a frequency different from a frequency at which background light is produced.

3. The apparatus of claim 2 wherein the excitation light source includes a mercury vapor lamp.

4. The apparatus of claim 3 wherein the light cycling means comprises:
   (a) a d.c. operating power supply;
   (b) control transistor means connected between the operating power supply and the lamp for applying operating power from the power supply to the lamp when in a biased condition and for blocking operating power to the lamp when in a nonconducting condition;
   (c) a switching means for producing a switching input to the control transistor means, the switching input determining whether the control transistor means resides in the biased condition or nonconducting condition; and
   (d) lamp ignition means connected to the lamp for providing a momentary ignition voltage across the lamp to initially ignite the lamp.

5. The apparatus of claim 4 wherein an output of the control transistor means to the lamp comprises a square wave voltage signal.

6. The apparatus of claim 1 wherein the excitation light source comprises:
   (a) a lamp for producing input light;
   (b) an objective lens for receiving the input light from the lamp and producing a collimated beam; and (c) excitation wavelength limiting means for removing undesirable wavelengths from the input light.

7. The apparatus of claim 6 wherein the excitation wavelength limiting means comprises a filtering lens.

8. The apparatus of claim 7 further comprising cooling means for cooling the filtering lens.

9. The apparatus of claim 8 wherein the filtering lens comprises a band pass filter centered to pass light having a wavelength of 253.7 nanometers and the excitation wavelength limiting means further comprises a dielectric mirror tuned to reflect light at 334 nanometers.

10. The apparatus of claim 6 wherein the excitation wavelength limiting means includes a monochromator.

11. The apparatus of claim 6 wherein the excitation light input mirror comprises a partially silvered mirror.

12. The apparatus of claim 1 wherein the excitation light input mirror comprises a dichroic mirror.

13. The apparatus of claim 12 wherein the dichroic mirror is adapted to reflect light at a wavelength of 253.7 nanometers and to pass light at wavelengths from 280 to 400 nanometers.

14. The apparatus of claim 1 wherein the returned light detecting means includes:
   (a) wavelength limiting means for passing returned light only at a desired wavelength; and
   (b) a photomultiplier tube adapted to produce a voltage signal representative of the intensity of light received by the tube.

15. The apparatus of claim 14 wherein the wavelength limiting means comprises a filter assembly and a dielectric mirror for blocking light at an excitation wavelength.

16. The apparatus of claim 14 wherein the wavelength limiting means comprises a monochromator.

17. The apparatus of claim 14 further comprising a background light filter for blocking ambient light.

18. A method of fluorescence spectroscopy comprising the steps of:
   (a) generating excitation light and directing the excitation light to an excitation light input mirror;
   (b) reflecting the excitation light with the excitation light input mirror to direct the reflected excitation light along a spectrometer light path;
   (c) reflecting the excitation light traveling along the spectrometer light path from a parabaloidal mirror having its focal point positioned at a near focal point of an ellipsoidal mirror;
   (d) reflecting the excitation light reflected from the parabaloidal mirror from the ellipsoidal mirror along a sample light path to a distant focal point of the ellipsoidal mirror, the distant focal point comprising a most sensitive sample position;
   (e) collecting fluorescent light emitted from the sample position along a path reciprocal to the sample light path;
   (f) reflecting the collected fluorescent light from the path reciprocal to the sample light path back along the spectrometer light path; and
   (g) receiving the collected fluorescent light reflected back along the spectrometer light path and producing an indication of the relative intensity of a desired wavelength constituent of the collected fluorescent light.

19. The method of claim 18 wherein the steps of collecting fluorescent light emitted from the sample position and reflecting the collected light back along the spectrometer light path comprise:
   (a) at the ellipsoidal mirror, collecting fluorescent light emitted from a sample position in response to the excitation light and reflecting the collected fluorescent light back along the spectrometer light path by reflection first from the ellipsoidal mirror and then from the paraboloidal mirror.

20. The method of claim 18 wherein the step of generating excitation light and directing the light to an excitation light input mirror comprises:

(a) chopping the excitation light at a frequency different from frequencies at which background light is emitted.

21. The method of claim 20 wherein the step of producing an indication of the relative intensity of a desired wavelength constituent of the collected fluorescent light includes:

(a) producing a chopped indication of relative intensity of collected fluorescent light each time the excitation light is chopped;

(b) producing a composite indication of relative intensity of collected fluorescent light each time the excitation light is produced; and (c) reducing the composite indication by the chopped indication to produce a true indication of the relative intensity of collected fluorescent light produced in response to the excitation light.

22. The method of claim 18 wherein the step of receiving the collected fluorescent light and producing an indication of the relative intensity of a desired wavelength constituent of the collected fluorescent light includes:

(a) removing undesired wavelengths from the collected fluorescent light; and (b) applying a selected portion of the collected fluorescent light to a photomultiplier tube.

23. A fluorescence spectrometer comprising:

(a) an excitation light source for directing excitation light along a spectrometer light path;

(b) a parabaloidal mirror positioned on the spectrometer light path to receive the excitation light;

(c) an ellipsoidal mirror having the focus of the parabaloidal mirror at a near focal point thereof, the ellipsoidal mirror being in position to receive excitation light reflected by the parabaloidal mirror and focus the excitation light along a sample light path to a distant focal point; and (d) returned light detecting means positioned on the spectrometer light path in position to receive returned light and providing an output indicating the intensity of a desired wavelength constituent of the returned light, the returned light including light which is reflected by the ellipsoidal mirror and parabaloidal mirror back along the spectrometer light path.

24. An apparatus for producing an excitation light beam for fluorescence spectroscopy, the apparatus comprising:

(a) a mercury vapor lamp;

(b) a d.c. operating power supply for supplying an operating voltage output;

(c) control transistor means connected between the operating power supply and the lamp and adapted to apply the operating voltage from the operating power supply to the lamp when in a biased condition and to block the operating voltage to the lamp when in a nonconducting condition;

(d) switching input means for producing a switching input to the control transistor means, the switching input determining whether the control transistor means is in the biased or nonconducting condition; and (e) lamp ignition means connected to the lamp for providing a momentary ignition voltage across the lamp to initially ignite.

25. A method of providing excitation light for fluorescence spectroscopy, the method comprising:

(a) producing a d.c. operating voltage;

(b) applying the d.c. operating voltage in square wave pulses to a preignited mercury vapor lamp at a chopped frequency different from a frequency at which background light is produced.

* * * * *